(12) United States Patent
Gnabs et al.

(10) Patent No.: US 8,552,229 B2
(45) Date of Patent: Oct. 8, 2013

(54) METHOD FOR UTILIZATION OF THE REACTION HEAT THAT OCCURS IN THE PRODUCTION PROCESS OF 1,2-DICHLOROETHANE FROM ETHYLENE IN A FLUIDIZED BED REACTOR

(75) Inventors: Ulrike Gnabs, Kelkheim/Taunus (DE); Michael Benje, Bad Soden (DE); Walter Kern, Kelkheim/Taunus (DE)

(73) Assignees: ThyssenKrupp Uhde GmbH, Dortmund (DE); Vinnolit GmbH & Co. KG, Burgkirchen (DE)

( * ) Notice: Subject to any disclaimer, the term of this patent is extended or adjusted under 35 U.S.C. 154(b) by 235 days.

(21) Appl. No.: 12/998,139

(22) PCT Filed: Sep. 2, 2009

(86) PCT No.: PCT/EP2009/006329
§ 371 (c)(1),
(2), (4) Date: Mar. 22, 2011

(87) PCT Pub. No.: WO2010/034392
PCT Pub. Date: Apr. 1, 2010

(65) Prior Publication Data
US 2011/0178345 A1    Jul. 21, 2011

(30) Foreign Application Priority Data
Sep. 23, 2008  (DE) .......................... 10 2008 048 526

(51) Int. Cl.
*C07C 17/00*     (2006.01)
*C07C 17/15*     (2006.01)

(52) U.S. Cl.
USPC ........................................... 570/216; 570/224

(58) Field of Classification Search
USPC .................................................. 570/216, 224
See application file for complete search history.

(56) References Cited

U.S. PATENT DOCUMENTS

| 4,368,173 A | 1/1983 | Jimenez et al. |
| 6,911,185 B1 | 6/2005 | Schön |

FOREIGN PATENT DOCUMENTS

| DE | 41 31 446 | 6/1993 |
| DE | 197 18 871 | 11/1998 |
| DE | 10 2006 049 546 | 4/2008 |
| EP | 0 997 187 | 5/2000 |

OTHER PUBLICATIONS

Konishi et al., JP abstract 62273923, 1986.*

* cited by examiner

*Primary Examiner* — Jafar Parsa
(74) *Attorney, Agent, or Firm* — Collard & Roe, P.C.

(57) ABSTRACT

With a method for utilization of the reaction heat that occurs in the production of 1,2-dichloroethane from ethylene, by reaction with oxygen and hydrochloride (oxychlorination), in a fluidized bed reactor, with dissipation of this reaction heat through cooling pipe bundles situated within the reactor, positioned in the fluidized bed, utilization of the heat is supposed to be improved, while simultaneously reducing the size of the corresponding system elements. This is achieved in that part of the reaction heat is dissipated by heating boiler feed water, whereby the heated boiler feed water is used to heat heat sinks in the production process.

4 Claims, 1 Drawing Sheet

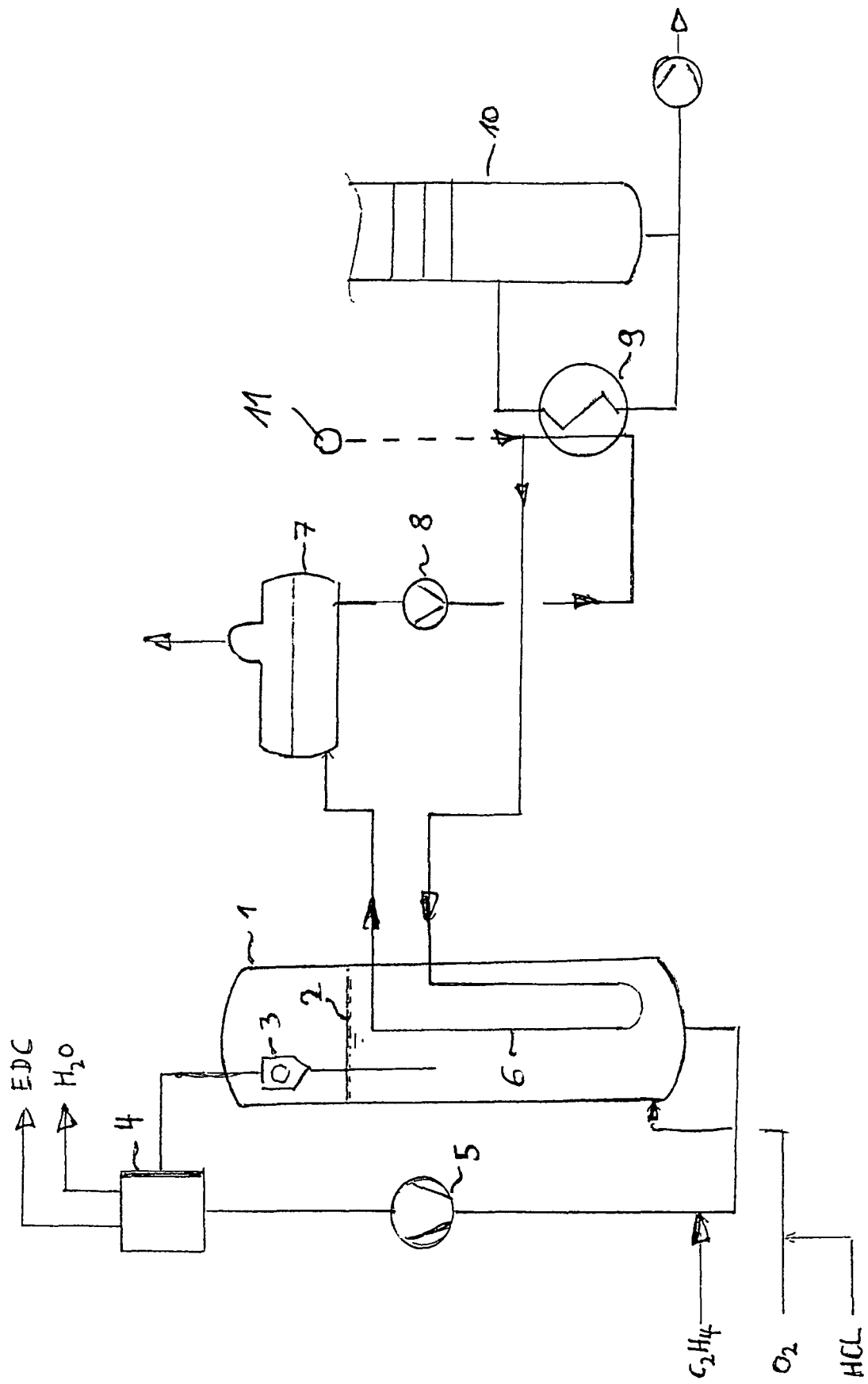

METHOD FOR UTILIZATION OF THE REACTION HEAT THAT OCCURS IN THE PRODUCTION PROCESS OF 1,2-DICHLOROETHANE FROM ETHYLENE IN A FLUIDIZED BED REACTOR

CROSS REFERENCE TO RELATED APPLICATIONS

This application is the National Stage of PCT/EP2009/006329 filed on Sep. 2, 2009, which claims priority under 35 U.S.C. §119 of German Application No. 10 2008 048 526.8 filed on Sep. 23, 2008, the disclosure of which is incorporated by reference. The international application under PCT article 21(2) was not published in English.

The invention is directed at a method for utilization of the reaction heat that occurs in the production of 1,2-dichloroethane (EDC) from ethylene, by means of reaction with oxygen and hydrochloride (oxychlorination), in a fluidized bed reactor, with dissipation of this reaction heat through cooling pipe bundles situated within the reactor, positioned in the fluidized bed.

Fluidized bed reactors for the oxychlorination of ethylene are cooled by means of cooling pipe bundles that are immersed in the fluidized bed (DE 197 18 871 A). Boiler feed water that is circulated is evaporated in these cooling pipe bundles. This steam is either given off toward the system boundary or used to heat columns or heaters in a facility network for the EDC/VCM process. In this connection, the aim is to produce steam of the highest possible quality, i.e. hot steam, since this is needed for heating purposes at various locations of the EDC/VCM process (for example for heating the VCM column). A solid bed reactor through which flow takes place radially, for carrying out heterogeneously catalytic gas phase reactions, i.e. a different reactor type, is known from DE 41 31 446 A1.

The construction size of an oxychlorination reactor is determined, on the one hand, by the required cooling surface for dissipating the reaction heat, and, on the other hand, by the amount of catalyst required for a specific EDC production amount, and the volume of the fluidized bed in the fluidized state is determined as a result of this. Based on the construction size of the cooling pipe bundle required for design reasons, the actual catalyst inventory of the reactor is always greater than would actually be necessary for a specific desired production amount, or the space/time yield that can actually be achieved with the catalyst is not implemented, for design reasons.

Fundamentally, two paths can be taken to reduce the size of the reactor or to increase the production amount at a given reactor volume, i.e. also for better utilization of the catalyst (process intensification):

1) Increasing the Reaction Temperature

An increase in the reaction temperature leads to an increase in the production amount (space/time yield), on the one hand, and to improved heat dissipation, on the other hand (by way of an increase in the effective temperature difference for the heat transfer from the fluidized bed to the cooling pipe bundle).

It is disadvantageous, in this connection, that when the reaction temperature is increased, the production loss as the result of secondary reactions, such as the formation of more highly chlorinated by-products or the oxidation of ethylene to $CO$ and $CO_2$ (a person skilled in the art speaks of ethylene burn-off) increases greatly, and impairs the efficiency of the process.

2) Increasing the Effective Temperature Difference

By means of an increase in the effective temperature difference, it is possible to significantly reduce the required cooling surface and thus the construction size of the cooling pipe bundle, and this also leads to a reduction in size of the reactor. The increase in the temperature difference can be achieved by means of a reduction in the pressure of the steam that is produced. This, however, leads to the result that a large amount of low-quality steam is produced, and this in turn worsens the efficiency of the process.

Likewise, the effective temperature difference can be increased in that the boiler feed water is super-cooled before entry into the cooling pipe bundle.

The heat transfer coefficient $\alpha_{aussen}$ (heat transfer from the fluidized bed to the outer cooling pipe wall) is significantly lower than the heat transfer coefficient $\alpha_{innen}$ (heat transfer from the inner cooling pipe wall to the cooling water), specifically not only in the case of pure convective heat transfer but also in the case of evaporation at the inside of the cooling pipe. For this reason, the total heat transfer coefficient K changes only little in the case of a partial or complete transition from evaporation cooling to convective cooling. The influence of the effective temperature difference on the amount of heat that can be transferred per surface area unit is clearly greater.

Super-cooling of the boiler feed water can take place in various ways; for example, super-cooling can take place in a heat exchanger, by means of air or water cooling. However, this variant is inefficient, since the heat can no longer be used.

Another variant is cooling of the boiler feed water by means of intermediate relaxation. Here, the boiler feed water is relaxed to a low pressure in an (additional) evaporation container, whereby a fixed amount of steam having a corresponding temperature is formed. This method is also economically disadvantageous, since low-quality steam is produced. Furthermore, additional equipment is needed, and the electrical energy consumption of the boiler feed water pump increases, since the boiler feed water has to be brought back to the starting pressure after the relaxation.

In order to meet the above problems, the task of the invention consists in improving the utilization of the heat, while simultaneously reducing the size of the corresponding system elements.

With a method of the type indicated initially, this task is accomplished, according to the invention, in that part of the reaction heat is dissipated by means of heating boiler feed water, whereby the heated boiler feed water is used for heating heat sinks in the production process of EDC, VCM, PVC, or in other heat sinks.

The advantage of the method of procedure according to the invention consists in that heat sinks in the EDC/VCM/PVC facility network are no longer heated with steam, as they were previously, but rather directly with heated boiler feed water. As a result, the boiler feed water cools off and can then be fed into the cooling pipe bundles of the oxychlorination reactor, once again, for renewed heating. As a result, the reaction heat of the oxychlorination is utilized further, and the efficiency of the process is retained. It is possible, in this connection, to dissipate the reaction heat completely, by heating boiler feed water, or to allow the boiler feed water to partly evaporate.

A particular advantage consists in that the wear on the cooling water side is significantly reduced, with a correspondingly reduced amount of steam, with an accompanying reduced flow velocity.

Examples of suitable heat sinks in the facility network of EDC/VCM/PVC production are:

| | |
|---|---|
| circulation evaporator | VCM column |
| circulation evaporator | HCl column |
| circulation evaporator | VCM stripper |
| circulation evaporator | low-boiler column |
| circulation evaporator | dehydration column |
| pre-heater | EDC (EDC splitting) |
| pre-heater | circulating gas (oxychlorination) |
| pre-heater | HCl (oxychlorination) |
| dryer | (PVC drying) |

However, the invention is not restricted to these examples.

Further embodiments, characteristics, and advantages are evident from the dependent claims. In this connection, it can be provided that distillation columns in the facility network for the production of 1,2-dichloroethane/vinyl chloride are heated by means of the boiler feed water heated by means of the reaction heat.

Another possibility, according to the invention, consists in that heat exchangers for heating process streams in the facility network for the production of 1,2-dichloroethane/vinyl chloride are heated by means of the heated boiler feed water, whereby according to the invention, it can also be provided that a drying device of polyvinyl chloride (PVC) is heated by means of the heated boiler feed water.

As already mentioned above, further heat sinks can also be heated up accordingly.

EXAMPLES

In an oxychlorination reactor, a thermal output of 19,221 kW is supposed to be transferred. The heat transfer takes place by means of cooling pipe bundles of 12 pipes each, at a length of 11.5 m, with an outside diameter of 88.9 mm, immersed in the fluidized bed.

1 Heat Transfer by Means of Evaporation

Boiler feed water at 186° C. is evaporated (steam pressure approximately 11.5 bar abs.). 400 W/m²K was determined as the total heat transfer coefficient. The reaction temperature (temperature of the fluidized bed) amounts to 215° C. With these data, it is possible to calculate a required heat exchange surface of 1657 m², which corresponds to approximately 43 cooling pipe bundles, from the required transfer output of 19,221 kW. In this connection, a thermal output of approximately 447 kW is transferred per cooling pipe bundle. At an evaporation enthalpy of the boiler feed water of 1992.5 kJ/kg, approximately 34.7 t steam/h are produced. From this, a circulation amount of approximately 434 t/h boiler feed water is obtained at an evaporation rate of 8%.

2 Heat Transfer by Means of Production of Hot Water

The thermal output of 19,221 kW/m² is predominantly supposed to be transferred by means of heating boiler feed water. 395 W/m²K was determined as the total heat transfer coefficient. The required circulation amount of boiler feed water that heats up to 186° C. with the available pipe length is determined by means of a numerical calculation method, in iterative manner. Using the same method, the thermal output transferred per cooling pipe bundle, in this connection, is calculated. This results in a boiler feed water amount of 10,093 t/h per cooling pipe bundle. A thermal output of approximately 320 kW/cooling pipe bundle is transferred by means of heating the boiler feed water. The required pipe length for heating the boiler feed water turns out to be approximately 70 m. This leaves 138−70=68 m available, which correspond to a heat exchange surface of 19 m².

A thermal output of 220 kW transferred by means of evaporation can be calculated with the heat transfer coefficient of 400 W/m² and the temperature difference of 29° C. (215−186). In total, therefore 320+220=540 kW can be transferred, corresponding to an increase of approximately 20%. If the entry temperature of the boiler feed water is lowered to 150° C., an increase in output of 44% can be determined in the same manner. The increases that can be achieved in this way can either be used in the planning of new facilities, to design reactors more efficiently, or to make existing facilities more efficient.

In the following, the invention is explained in greater detail, using the drawing, as an example. This drawing shows a facility using the method according to the invention, in a simplified representation, as a facility schematic.

In the oxychlorination reactor designated as 1, there is a fluidized bed 2, from which the product of the product separation 4 is fed in, by way of a reactor cyclone 3 or a corresponding catalyst separator.

In this connection, 5 refers to a circulating gas compressor that circulates the circulating gas back into the oxychlorination reactor, whereby the corresponding educts are also fed into this reactor.

It is essential to the invention that cooled boiler feed water from an evaporation vessel 7 is applied to the cooling pipe bundle designated as 6, whereby the boiler feed water is circulated by way of the pump 8.

In the example shown—without the invention being restricted to this—the boiler feed water gives off its heat to a circulation evaporator 9 of a distillation column 10, and is thereby cooled in the manner according to the invention. The feed of boiler feed water is further designated with 11.

As was already mentioned above, the invention is not restricted to this example. Other system elements can also be heated by way of the boiler feed water.

The invention claimed is:

1. Method for utilization of the reaction heat that occurs in the production of 1,2-dichloroethane from ethylene, by means of reaction with oxygen and hydrochloride (oxychlorination), in a fluidized bed reactor, with dissipation of this reaction heat through cooling pipe bundles situated within the reactor, positioned in the fluidized bed, wherein
  a part of the reaction heat is dissipated by means of heating boiler feed water, whereby the heated boiler feed water is used to heat heat sinks in the production process.

2. Method according to claim 1, wherein
  distillation columns in the facility network for the production of 1,2-dichloroethane/vinyl chloride are heated by means of the boiler feed water heated by means of the reaction heat.

3. Method according to claim 1, wherein
  heat exchangers for heating process streams in the facility network for the production of 1,2-dichloroethane/vinyl chloride are heated by means of the heated boiler feed water.

4. Method according to claim 1, wherein
  a drying device for polyvinyl chloride (PVC) is heated by means of the heated boiler feed water.

* * * * *